(12) United States Patent
Fouillet et al.

(10) Patent No.: US 9,474,661 B2
(45) Date of Patent: Oct. 25, 2016

(54) ITEM INTENDED TO COME INTO CONTACT WITH A LIQUID, IN PARTICULAR A BANDAGE

(71) Applicants: COMMISSARIAT A L'ENERGIE ATOMIQUE ET AUX ENERGIES ALTERNATIVES, Paris (FR); LABORATORIES URGO, Chenove (FR)

(72) Inventors: Yves Fouillet, Voreppe (FR); Cyril Marsiquet, Roumazieres Laubert (FR); Frederic Revol-Cavalier, Seyssins (FR); Jean-Marc Pernot, Dijon (FR); Serge Lecomte, Dijon (FR); Michel Lamoise, Bessey les Citeaux (FR)

(73) Assignees: Commissariat a l'Energie Atomique et aux Energies Alternatives, Paris (FR); Laboratoires Urgo, Chenôve (FR)

( * ) Notice: Subject to any disclaimer, the term of this patent is extended or adjusted under 35 U.S.C. 154(b) by 0 days.

(21) Appl. No.: 14/416,928

(22) PCT Filed: Jul. 22, 2013

(86) PCT No.: PCT/IB2013/056010
§ 371 (c)(1),
(2) Date: Jan. 23, 2015

(87) PCT Pub. No.: WO2014/016759
PCT Pub. Date: Jan. 30, 2014

(65) Prior Publication Data
US 2015/0209200 A1    Jul. 30, 2015

(30) Foreign Application Priority Data
Jul. 23, 2012 (FR) ...................... 12 57108

(51) Int. Cl.
*A61F 13/00* (2006.01)
*A61F 13/537* (2006.01)
(Continued)

(52) U.S. Cl.
CPC ..... *A61F 13/5376* (2013.01); *A61F 13/00029* (2013.01); *A61F 13/00034* (2013.01);
(Continued)

(58) Field of Classification Search
CPC ............. A61F 13/0213; A61F 13/022; A61F 13/0226; A61F 2013/00225; A61F 2013/00229; A61F 2013/00246; A61F 2013/00251; A61F 2013/00748; A61F 2013/00523; A61F 2013/00608; A61F 2013/00757; A61F 2013/0074; A61F 2013/00744; A61F 13/0203; A61F 13/0206; A61F 13/0209; A61F 2013/530941; A61F 13/5323; A61F 13/53713; A61F 2013/00544; A61F 13/00029; A61F 13/00068; A61F 2013/00727; A61F 2013/00731; A61F 2013/53051
See application file for complete search history.

(56) References Cited

U.S. PATENT DOCUMENTS

| 4,676,785 A | 6/1987 | Battista .................... 604/369 |
| 2004/0127833 A1 | 7/2004 | Sigurjonsson .............. 602/41 |

FOREIGN PATENT DOCUMENTS

| EP | 0875222 | 11/1998 |
| EP | 1974705 | 10/2008 |
| WO | WO00/16725 | 3/2000 |

*Primary Examiner* — Peter S Vasat
(74) *Attorney, Agent, or Firm* — Norton Rose Fulbright US LLP

(57) ABSTRACT

The present invention relates to an item (10) having liquid (L) storage and/or discharge properties, in particular a bandage, comprising: —a liquid-permeable proximal structure (20), consisting of a material capable of inflating in the presence of liquid (L), —a distal structure (30) capable of draining a liquid (L), —a hydrophobic and non-absorbent spacer structure (40) extending between the distal (30) and proximal (20) structures, and being capable of locally limiting, when said material is not inflated, the exchange of liquid between the distal and proximal structures by maintaining a gap between said structures, and of authorizing a local expansion of the proximal structure in at least one zone (P) where said material is inflated in response to coming into contact with a liquid, said expansion causing the proximal and distal structure to move together locally and the transfer of said liquid from the zone of the proximal structure (20) having undergone expansion to the distal structure (30).

29 Claims, 5 Drawing Sheets

Figure 1:
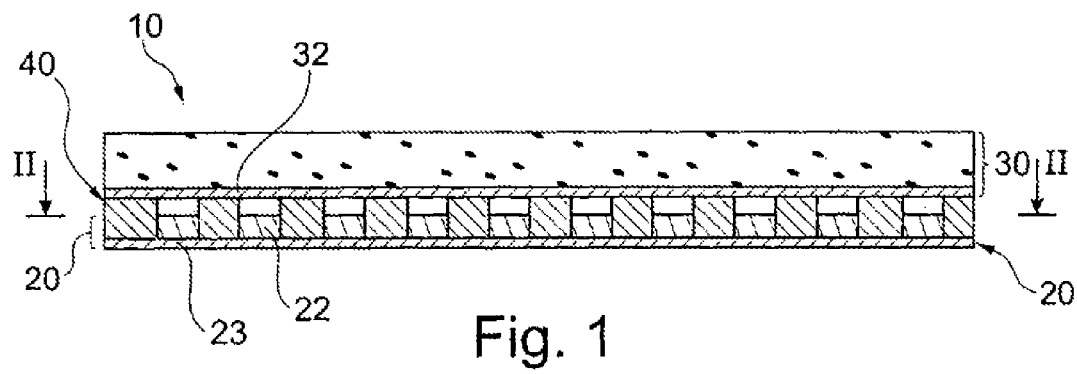

(51) Int. Cl.
    *A61F 13/532*      (2006.01)
    *A61F 13/535*      (2006.01)
    *A61F 13/02*      (2006.01)
    *A61L 15/22*      (2006.01)
    *A61L 15/42*      (2006.01)
    *A61L 15/60*      (2006.01)
    *A61F 13/511*      (2006.01)
    *A61F 13/53*      (2006.01)

(52) U.S. Cl.
CPC ... *A61F13/00046* (2013.01); *A61F 13/00051* (2013.01); *A61F 13/00068* (2013.01); *A61F 13/022* (2013.01); *A61F 13/0209* (2013.01); *A61F 13/0213* (2013.01); *A61F 13/535* (2013.01); *A61F 13/5323* (2013.01); *A61F 13/53713* (2013.01); *A61L 15/225* (2013.01); *A61L 15/425* (2013.01); *A61L 15/60* (2013.01); *A61F 2013/00544* (2013.01); *A61F 2013/00548* (2013.01); *A61F 2013/00748* (2013.01); *A61F 2013/51191* (2013.01); *A61F 2013/53089* (2013.01); *A61F 2013/530562* (2013.01); *A61F 2013/530846* (2013.01); *A61F 2013/530956* (2013.01)

ITEM INTENDED TO COME INTO CONTACT WITH A LIQUID, IN PARTICULAR A BANDAGE

CROSS-REFERENCE TO RELATED APPLICATIONS

This application is a national phase application under 35 U.S.C. §371 of International Application No. PCT/IB2013/056010 filed 22 Jul. 2013, which claims priority to French Patent Application No. 1257108 filed 23 Jul. 2012. The entire contents of each of the above-referenced disclosures is specifically incorporated herein by reference without disclaimer.

The present invention relates to items intended to come into contact, via their proximal side, with liquids, in particular liquids secreted by the skin, the wound and/or the mucous membranes, for managing the propagation and storage of these liquids, and more particularly, but not exclusively, dressings to be applied to a wound.

The management of the propagation of liquids and also their storage are complex problems to be solved for which the items proposed in the field of dressings and hygiene products does not at the current time provide entirely satisfactory solutions.

These items must in fact satisfy specifications which comprise antagonistic properties. A first requirement is to move the liquids away as far as possible and as rapidly as possible in order to prevent, because of their accumulation, any phenomenon of maceration or irritation at the level of the skin, the wound or the mucous membranes. The liquids must not accumulate, but it is also preferable to avoid their lateral migration from the site of secretion in order to reduce the increase in the moistened area for the purposes of guaranteeing better hygiene and in the interests of user comfort.

This is particularly important when a dressing is used. In this case, it is important to prevent the skin located at the edge of the lesion, called perilesional skin, which is very delicate, from being wet since this may cause a modification of the skin, promoting for example an infection and/or irritation.

Thus, it is desirable for the dressing to efficiently drain the body liquids secreted by the wound and in particular to prevent lateral migration of these liquids from their site of secretion to the periphery of this site. Such drainage makes it possible to keep the periphery of the wound dry, whence better hygiene and improved healing conditions.

A second requirement is to store these liquids and to prevent their return to the skin, the wound or the mucous membranes. Significant storage makes it possible to increase the duration of use of the item. In the case of a dressing, this duration of use is particularly important since the risk of impairing the wound healing process is reduced by changing said dressing less frequently. However, the optimization of the storage capacities results, because of the accumulation of the liquids, in thicker and heavier items for which the risks of leaking, of detachment because of the weight of the item, for example because of the vertical positioning of the dressing on a leg ulcer, and of return of the liquids from the storage zone to the skin, the wound or the mucous membranes increase. In point of fact, it is also desirable to have products which are as thin and as flexible and conformable as possible in order to fit the anatomy of the area of the body to which they are applied.

It would therefore be desirable to have items which make it possible to manage the propagation and the storage of liquids, in particular liquids secreted by the wound, the skin or the mucous membranes, by distancing said liquids from their point of secretion in order to prevent their accumulation but also their lateral migration and their return to the skin, the wound or the mucous membranes. In the case of a dressing, it would in addition be desirable, in an optimum version, for it to be possible for said dressing, in order to be as thin and conformable as possible, to dispense with the drawbacks associated with the presence of a storage layer, which would make it possible to reduce, or even eliminate, the necessity of periodically changing it.

The invention aims precisely to produce items and in particular dressings which meet these objectives.

The invention also seeks to perfect hygiene items other than dressings, such as disposable diapers or feminine hygiene items, by offering a high capacity for absorption of leaking body fluids, without this absorption capacity being detrimental to user comfort.

Application US2004/0127833 discloses a method for producing a dressing, comprising an absorbent structure in which discrete cavities which receive an absorbent material are formed. These cavities aim only to reinforce the storage capacity of the dressing, and do not make it possible to satisfactorily meet the objectives indicated above.

U.S. Pat. No. 4,676,785 describes an item in which the swelling of a material following the introduction, on the proximal side, of a liquid from an aperture causes a valve member to close this aperture. The cells containing the water-swellable material are borne by an impermeable basic film which constitutes a distal structure relative to the liquid emission zone. There is no transfer of liquid from the face of the item located on the fluid emission side to the distal structure.

Application EP 1 974 705 A1 describes an item comprising a proximal structure in contact with the skin and a distal structure formed from an impermeable film. There is expansion, following the absorption of a liquid, of a material present in a cavity of the item, but this expansion does not result in the transfer of liquid to the distal structure.

In these two documents, the material capable of swelling is present opposite the aperture for the liquid in the cavity which contains it.

Application EP 0 875 222 describes an item which involves an absorbent layer that can swell under the effect of water absorption, its expansion causing the opening of slits in contact with a wound.

A subject of the invention, according to a first of its aspects, is an item having liquid discharge and/or storage properties, in particular a dressing, comprising:
  a liquid-permeable proximal structure, comprising a material capable of swelling in the presence of the liquid,
  a distal structure capable of draining a liquid, and
  a hydrophobic and nonabsorbent insert structure, preferably with openings, said structure extending between the distal and proximal structures, and being capable of locally limiting, when said material is not swollen, the exchange of liquid between the distal and proximal structures by maintaining a gap between these structures, and of allowing a local expansion of said proximal structure in at least one zone where said material swells in response to coming into contact with a liquid, this expansion causing the proximal structure and the distal structure to move closer together locally and the transfer of said liquid from this zone of the proximal structure having undergone the expansion to the distal structure.

When there are openings in the insert structure, the expansion may take place within said openings, and transfer by capillary action may occur by contact between the proximal and distal structures through the openings.

According to the invention, the item is capable of efficiently discharging the secretions right where they are emitted, by draining them to the distal structure. Furthermore, the region where the item covers the skin, the wound and/or the mucous membranes but where there is no secretion emitted is not affected by the liquid present in the distal structure, since said liquid cannot descend back towards the proximal structure because of the presence of the insert structure.

Unlike the teachings of U.S. Pat. No. 4,676,785 and EP 1 974 705 A1, there may be drainage of the liquid to a distal structure, where this liquid may continue to be drained. This drainage may take place without being accompanied by the closing of a valve member. The material may be initially located, in the item, closer to the surface for admission of the liquid in the item than to the opposite side.

The term "capable of draining" is intended to describe an ability to store a liquid, to spread it out or to transfer it by lateral diffusion.

The term "lateral diffusion" should be understood to mean diffusion in a direction substantially perpendicular to the direction in which the thickness of the item is measured, that is to say substantially parallel to the surface on which the item is placed when it is used.

The term "material capable of swelling" should be understood to mean a material which experiences an increase in its volume in the presence of water, for example of at least 10%, better still 200%, or even 500% or 3000%. It may be a material composed of a superabsorbent polymer or comprising such a polymer.

The term "material" denotes a single material or a set of different materials which are combined together, in which case the material is, for example, a composite material comprising a superabsorbent material mixed with or placed between one or more other materials, serving as a support for the superabsorbent material.

The material capable of swelling may thus be a hydrocolloid which swells on contact with liquids, in the form of a powder, of granules or of fibers, a water-swelling alveolar material such as, for example, a hydrophilic polyurethane foam or a hydrophilic gel such as, for example, a hydrophilic polyurethane gel. As examples of a hydrocolloid, mention may be made of cellulose derivatives such as, for example, alkali metal salts of carboxymethylcellulose, alginates or superabsorbent polymers (SAPs).

By way of superabsorbent polymer (SAP), use may be made of one or more polymers capable, for example, of absorbing from 10 to 50 times their weight of water (representative of a physiological liquid), and of not releasing the water in the event of moderate pressure on said polymers. The water absorption capacity is due to the powerful interaction between the water molecules and hydrophilic groups of the polymer, in particular capable of establishing a hydrogen bond. The superabsorbent polymers may be chosen in particular from starch-based grafted copolymers, crosslinked derivatives of carboxymethylcellulose and modified hydrophilic polyacrylates. More particularly, they may be hydrolyzed starch/acrylonitrile copolymers, neutralized starch/acrylic acid copolymers, saponified copolymers, esters of acrylic acid and vinyl acetate, hydrolyzed acrylonitrile copolymers, acrylamide copolymers, modified crosslinked polyvinyl alcohols, crosslinked polyacrylate salts, neutralized and crosslinked polyacrylic acid, carboxylated cellulose, or a mixture thereof.

Generally, this material is used in the pulverulent state and it is only in contact with a fluid, in the case in point a physiological liquid, that it will form a gel having retention properties.

By way of preferred superabsorbent materials, mention may more particularly be made of sodium polyacrylates such as, for example, those sold under the name Favor®-Pac 230 or Luquasorb® 1161.

By way of water-swelling alveolar material, use may also be made of a hydrophilic polyurethane (PU) foam like, for example, that sold under the name MCF.03 by the company Advanced Medical Solution (AMS).

As composite material, mention may be made of materials consisting of the abovementioned hydrocolloids incorporated into a matrix based on a polymer-based formulation, such as, for example, the hydrocolloid adherent compositions used in the dressings or stoma field, or a textile material such as, for example, the absorbent nonwovens incorporating SAP particles, commonly used in the hygiene field.

Use is preferably made of nonwovens obtained by the dry production method known as "airlaid", which contain SAP particles and in particular between 20% and 60% by weight of SAP relative to the total weight of the nonwoven. Such nonwovens are, for example, sold by the company EAM Corporation under the reference Novathin®. According to one preferred embodiment of the present invention, use is made of a nonwoven based on superabsorbent polymer particles and on cellulose fibers without incorporation of thermal bonding materials or of latex and which is covered on each of its faces with a cellulose-based web.

According to another variant of the present invention, it is also possible to use, as composite material, a material consisting of two cellulose-based webs between which are incorporated particles of superabsorbent polymers, alone or in combination with binders.

According to the applications of the present invention, it is preferred to use a material capable of swelling which has reversible swelling properties, i.e. which, during drying, shrinks and returns for example to approximately its initial volume, such as, for example, a hydrophilic polyurethane foam or a material based on SAP particles.

Generally, during use in a dressing, a material compatible with sterilization and suitable for this use, in particular from the point of view of its innocuousness, is chosen.

It is desirable for the proximal structure to be designed such that the liquid does not migrate (or barely migrates) laterally in said structure from the zone(s) where the secretions are emitted, so that the swelling of said material takes place essentially only opposite the zone(s) where the secretions are emitted.

The proximal structure has a nonuniform distribution of the material capable of swelling, in particular a matrix distribution according to its plane, for example with a gap ranging from 1 mm to 20 mm between the regions where the material capable of swelling is present. The distribution of the material capable of swelling is discrete, i.e. the regions where the material capable of swelling is present do not touch one another.

The material capable of swelling may be held on the item in various ways. To this effect, it is preferable for the proximal structure to comprise a permeable substrate, which serves as a support layer for the material capable of swelling. This permeable support layer must limit, or even prevent, the lateral migration of exudates. It also serves as an interface layer, intended to come into contact with the skin, with the wound or with the mucous membranes.

Generally, the support layer comprises a material which is permeable, but sparingly or non absorbent.

By way of permeable materials, mention may be made of nonabsorbent textile materials such as knits, wovens or nonwovens. Nonabsorbent nonwovens will preferably be used. The nonwoven may be any type of nonwoven commonly used in the hygiene and dressings field, in particular a spun laid, carded or spun lace nonwoven commonly denoted using the terms web or coverstock. Its grammage is preferably between 5 and 50 $g/m^2$, preferably between 20 and 40 $g/m^2$. The textile material is nonabsorbent in the sense that it does not contain absorbent fibers such as rayon, viscose or cellulose derivatives, and that it does not contain absorbent particles. It may comprise, for example, polyamide, polyester and/or polyolefin fibers.

The web may be hydrophilic or hydrophobic, but a hydrophobic web will be preferred. According to one embodiment, the web comprises polyethylene fibers. A spunlaid nonwoven will, for example, be chosen, preferably of hydrophobic spunbond type sold by the company Fiberweb under the name Berotex® PE-SX, or a hydrophilic carded nonwoven comprising polyester and polyethylene fibers, sold by the company Sandler under the name Sawabond® 4383.

The nonabsorbent web preferably consists of hydrophobic fibers, but it may also consist of hydrophilic fibers and have undergone a treatment in order to make it hydrophobic. Conversely, it may consist of hydrophobic fibers and may undergo a treatment to make it hydrophilic. The web may consist of several layers in so far as its permeability is sufficient.

The support layer may consist of a single material or of a juxtaposition of different materials, in which case the term composite material is used.

As other permeable materials, mention may be made of perforated or microperforated materials, for instance perforated plastic films (for example based on polyurethane or on polyethylene), or 3D films such as the products sold by the company Tredegar Film Products. These materials are well known to those skilled in the art and are commonly used in the hygiene field. It is also possible to use, as permeable materials, dressings known as "interface dressings", such as, for example, the products sold by the companies Laboratoires Urgo and Molnlycke Health Care respectively under the names Urgotul® and Mepitel®.

Finally use may be made of perforated layers of formulations which are hydrophobic or hydrophilic but nonabsorbent or sparingly absorbent, based on polymers. These formulations may be adherent or nonadherent. In the case of dressings, use will preferably be made of microadherent or nonadherent formulations which make it possible not to impair the healing process when removed from the wound.

Such formulations are well known to those skilled in the art and are, for example, produced based on silicone gel(s), on pressure-sensitive silicone adhesive(s) or on compositions containing a block elastomer of the poly (styrene-olefin-styrene) type, a plasticizer such as a mineral oil and a small amount of hydrocolloid(s) so as to create a moist environment for promoting the healing process without making the composition absorbent in order to avoid blocking the holes. Such microadherent formulations are, for example, used in the dressings sold by the company Laboratoires Urgo under the names Urgoclean® and Urgotul Absorb®.

According to possible variants, these interface dressings and these perforated layers of hydrophobic or hydrophilic formulations may be combined with the abovementioned permeable materials, in particular the nonabsorbent nonwovens.

In one example of implementation of the invention, the material capable of swelling is supported by a permeable support layer, which is preferably hydrophobic as detailed above, and is for example attached to the face of this layer which is facing the insert structure. In one variant, the material capable of swelling is present between two layers of the proximal structure, and is for example trapped therein by cavities formed by the assembly of these layers.

The material capable of swelling may be integrated into the item, during the production thereof, in a nonpulverulent form, for example in the form of inserts such as pellets or aggregates, the largest dimension of which is, for example, greater than or equal to 1 mm and less than or equal to 15 mm. These inserts may, where appropriate, be made of a composite material comprising a superabsorbent polymer in pulverulent form. In one example of implementation of the invention, the material capable of swelling is thus incorporated into the item after being cut from a sheet, for example by means of a punching operation which makes it possible to form the abovementioned pellets, the latter having, for example, a circular or polygonal, preferably regular, outline.

In other examples of implementation of the invention, the material capable of swelling is incorporated into the item, during the production thereof, in pulverulent form, preferably with a nonuniform distribution, for example in the form of clusters which are localized like the openings of the insert structure.

The proximal structure may comprise at least one support layer, as described above, for holding the material capable of swelling on the item, the support layer(s) being produced so as not to impede the expansion of the material capable of swelling in the direction of the distal structure, while at the same time preferably impeding the expansion in the opposite direction. As a variant, the proximal structure is made up of only the material capable of swelling, the function of supporting the material capable of swelling being provided by the insert structure. In this case in particular, the material capable of swelling may be incorporated in a discontinuous form into the item, for example in the form of inserts such as pellets housed in openings of the insert structure. In this case in particular, the insert structure may come into contact with the skin, the wound or the mucous membranes. Preferably, the item, in particular in the case of a dressing, comprises a layer of interface with the wound which is continuous and extends over the entire lower face of the item liable to come into contact with the wound. This interface layer may or may not serve to hold the material capable of swelling on the item. The interface layer may be of use for limiting, or even preventing, the expansion of the proximal structure in the direction of the skin and/or of the mucous membranes. The inserts may be borne by the interface layer when the latter is placed against the insert structure.

The proximal structure may be entirely located outside the insert structure in the absence of swelling of the material capable of swelling. As a variant, the proximal structure is inserted in the insert structure in the absence of swelling of the material capable of swelling, extending over only a part of the thickness thereof.

The proximal structure comprises, for example, the material capable of swelling in the form of inserts, said material preferably being a nonwoven in which particles of a superabsorbent are imprisoned, the insert structure comprising openings in which the inserts are at least partially inserted, the inserts structure having a sufficient thickness so that, before swelling, the inserts do not come into contact with the distal structure, the insert structure having in particular a thickness greater than that of the inserts, and sufficiently small for the swelling of the inserts to bring them into contact with the distal structure.

The insert structure is hydrophobic and nonabsorbent, so as to fluidically isolate the proximal and distal structures at the place where no expansion of the proximal structure takes place. It must also prevent the lateral migration of the liquid and, in the case where it has openings, prevent the liquid from passing laterally from one opening to another. Preferably, it is flexible so as to be able to conform to the anatomical contours. The insert structure is, for example, a closed-cell alveolar material in the form of a layer of a foam made of a thermoplastic material, in particular a polyolefin, for example polyethylene, or an assembly of several layers of this type. It may also be in the form of a film, a textile material or a layer, which are hydrophobic and nonabsorbent, based on adhesives, on polymers or on elastomers such as polyurethane, polydimethylsiloxane and its variations (generally denoted under the generic term "silicone"), polyolefins (such as, for example, polyethylene), polyphenylene ether or formulations based on block polymers, for example of the (styrene-olefin-styrene) or (styrene-olefin) type, combined with a plasticizer.

The thickness of the insert structure is, for example, between 0.5 mm and 4 mm for an item constituting a dressing. When the material capable of swelling is present in the form of inserts within the insert layer, the thickness of said layer is greater than that of the inserts.

The insert structure preferably has openings, as previously mentioned, and the expansion of the proximal structure then at least partially takes place in an opening of the insert structure. Thus, the distribution of the openings of the insert structure is advantageously substantially the same as that of the material capable of swelling, so that the regions where this material is present may superimpose on the openings, preferably in a manner centered within each opening. The openings may have any shape. The openings may be formed by cutting from a sheet, online during the production of the item, or may be cut during a prior operation. The openings may or may not all have the same outline, with for example a regular or irregular distribution of the openings. The openings may have a circular or polygonal, in particular regular polygonal, outline. The openings may have a cross section which is constant throughout the thickness of the insert structure, or as a variant may have a cross section which varies, in particular decreases in the direction of the proximal structure, so as to promote the expansion thereof in the direction of the distal structure rather than in the opposite direction. In order to obtain a cross section which decreases, it is possible to use, for example, several sheets in which the openings are cut with decreasing sizes, and then to assemble said sheets. It may also be possible to cut the openings directly with the desired shape, for example using a laser.

The distal structure is capable of draining the liquids, i.e. it makes it possible to store them, to transfer them and/or to spread them out.

In one example of implementation of the invention, the distal structure comprises a layer forming a reservoir, having a water absorption capacity greater than or equal to 500 $g/m^2$, or even 800 $g/m^2$. The layer forming a reservoir may superimpose on the insert structure. The layer forming a reservoir may consist of any material capable of storing liquids, such as, for example, the absorbent layers commonly used in the hygiene and dressings field. By way of example, mention may be made of absorbent foams and preferably hydrophilic polyurethane foams and all the SAP-based materials previously mentioned, absorbent textiles such as, for example, viscose-based, rayon-based or cellulose-based nonwovens, such as, for example, cotton wool or hydrogels.

In another example of implementation of the invention, the distal structure is devoid of a layer forming a reservoir having a water absorption capacity greater than or equal to 500 $g/m^2$. In this case, the distal layer consists of a layer which allows lateral diffusion of the liquid in order to spread it out or to promote its transfer. The liquid is then, for example, discharged toward a layer forming a reservoir located at the periphery of the insert structure or toward a free end part where the liquid may evaporate.

When the layer forming a reservoir is located at least partially on the side of the insert structure, an item which is thinner and has an equivalent absorption capacity may be obtained. In one example of implementation, the layer forming a reservoir extends all around the insert structure. The item advantageously comprises, when the layer forming a reservoir is located on the side of the insert layer, a layer forming a barrier, located between the skin and/or the mucous membranes and the layer forming a reservoir, which is impermeable to water. When the layer forming a reservoir is located on the side of the insert structure, the liquid is conveyed into this layer forming a reservoir by a transfer layer which constitutes all or part of the distal structure. An external protective layer may cover this transfer layer and the layer forming a reservoir. Preferably, use will be made of the combination of a lateral diffusion layer and a reservoir layer for promoting the absorption of the liquid by the reservoir layer by virtue of a large area of contact between these two layers.

Materials which enable liquids to be spread out and/or to be transferred by lateral diffusion are commonly used in the hygiene and dressings field.

Mention may thus be made of textile materials such as knits, wovens and quite particularly nonwovens. These textile materials may be hydrophobic or hydrophilic, based on absorbent or nonabsorbent fibers. Among nonwovens, hydrophilic nonwovens will be preferred, and in particular those based on absorbent fibers, such as viscose or cellulose, combined with nonabsorbent fibers such as, for example, polyester or polyolefin fibers. By way of example of such nonwovens, mention may be made of the products sold respectively by the companies Suominen Corp and Orsa under the names Fibrella® 2000 and Jettex® 1205 c.

As other materials, mention may also be made of papers or microstructured films, the channels of which enable liquids to spread out and to migrate.

The insert structure may provide the attachment of the proximal structure to the distal structure, and in particular can comprise or be in the form of a water-impermeable adhesive layer extending discontinuously between the distal structure and the proximal structure, so as to make at least one opening devoid of adhesive where the swelling of the material of the proximal structure results in a transfer by capillary action of the liquid to the distal structure by contact between the proximal structure and the distal structure under the effect of said swelling.

The distal structure may comprise at least one cavity which opens out in the direction of the proximal structure, this cavity being at least partially superimposed on a zone of the proximal structure, where the swelling is liable to take place, and preferably being at least partially superimposed on an opening of the insert structure. The presence of such a cavity may make it possible to locally distance the proximal structure from the distal structure in the absence of swelling and may make it possible to reduce the thickness of the insert structure or to increase that of the proximal structure at the site where the material capable of swelling is present.

The insert structure may comprise two layers with openings, including one lower layer on the side of the proximal structure and one upper layer on the side of the distal structure, the openings of the upper layer having a smaller cross section than the openings of the lower layer, and being superimposed on the latter. The material capable of swelling may be at least partially contained, when dry, in the openings of the lower layer. The material capable of swelling may or may not entirely fill the openings of the lower layer. Such a variant may facilitate the holding in place of the material capable of swelling. Furthermore, a staged form of the cavity containing the material capable of swelling may increase the water sensitivity of the fluidic interrupter formed with this material, since, at equal expansion volume of the material compared with a cavity of constant cross section and of the same height and with the same amount of initial material, the presence of a narrower upper part makes it possible to increase the distance by which the material moves in the direction of the distal structure, and therefore to more rapidly contact said structure.

The openings of the lower layer preferably have a larger dimension, in particular a diameter, of between 5 and 25 mm, and the openings of the upper layer preferably have a larger dimension, in particular a diameter, of between 1 and 10 mm.

Preferably, the material capable of swelling is retained in the openings of the lower layer without the use of adhesive on the side of the proximal structure.

The material capable of swelling may advantageously be pasty, at least during the preparation of the item, in particular during its introduction into openings of the insert structure. This may facilitate its placing in the openings by spreading and scraping.

The material capable of swelling may comprise a water-expandable polymer, in particular based on SAP particles, and a water-soluble binder, in particular based on polyvinylpyrrolidone and/or on hydroxypropylcellulose.

The material capable of swelling may in particular have the following formulation, expressed by weight relative to the total weight of the mixture:
from 10% to 90% of water-expandable polymer(s), in particular based on SAP particles,
from 1% to 20% of water-soluble binder(s), for example based on polyvinylpyrrolidone and/or on hydroxypropylcellulose,
from 0% to 20% of glycerol, and
from 30% to 80% of homogenization liquid, in particular based on alcohol, preferably ethanol.

The distal structure may comprise a plurality of cavities arranged according to a matrix distribution, the cavities preferably being distributed like the zones of the proximal structure which are capable of swelling. The depth of the cavity or cavities is preferably less than the thickness of the distal structure, and between, for example, 10% and 90% of the thickness of the distal structure.

The item preferably constitutes a dressing, packaged in the sterile state, but as a variant may also constitute a disposable diaper or a feminine hygiene item. When the item is a dressing, besides the three structures previously defined (proximal structure, intermediate structure, distal structure), the dressing preferably comprises additional layers in order to guarantee that it is aseptic before and during use. Thus, on the wound side, depending on the nature of the interface layer, in particular if it is based on an interface dressing or a formulation based on polymers, it may comprise a temporary protector able to be removed before use. On the opposite side, it is covered with a layer that is impermeable to bacteria and to water but permeable to water vapor so as to promote the evaporation of liquids, termed external protective layer. Such layers are commonly used in the production of dressings and, for example, consist of polyurethane films such as the films sold by the company Exopack Advanced Coating under the name Inspire. Such a film may be assembled to the dressing by means, for example, of a discontinuous adhesive so as not to affect the permeability of the film to gases and in particular to water vapor. It may also be assembled to the proximal structure at the periphery of the dressing.

In the version where the transfer strip has a length greater than that of the insert structure, it is advantageously covered with such an external protective layer, so as to prevent the exudates present in the layer from soiling the area around the wound and also to prevent risks of external contamination of the dressing by bacteria.

Thus, according to one of its aspects, the invention relates to a device for transferring a liquid, comprising:
a liquid-permeable proximal structure intended to come into contact with the liquid,
a liquid-permeable distal structure, and
a hydrophobic and nonabsorbent insert structure placed between the proximal structure and the distal structure, said proximal structure comprising a material capable of swelling under the effect of liquids, such that the swelling of said material reduces the distance between the proximal structure and the distal structure, the liquid then being capable of passing from the proximal structure to the distal structure, through the insert structure.

Figure 2:
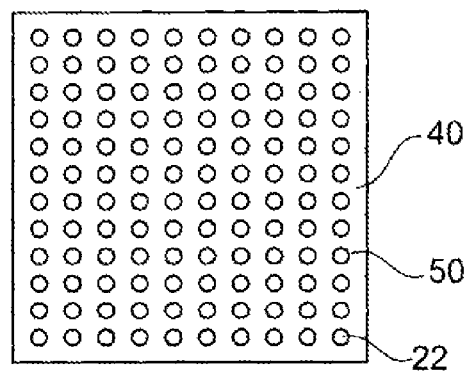
Figure 3:
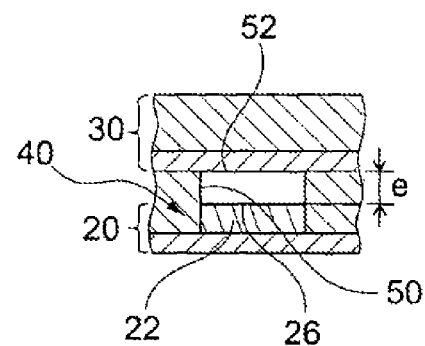
Figure 4:
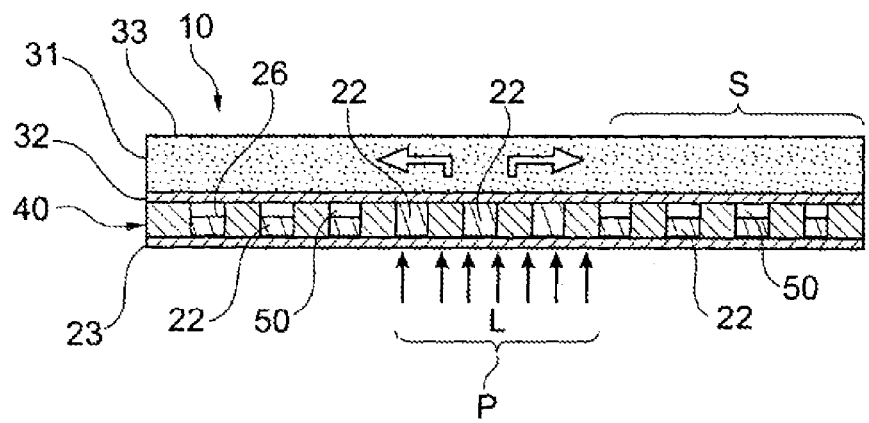
Figure 6:
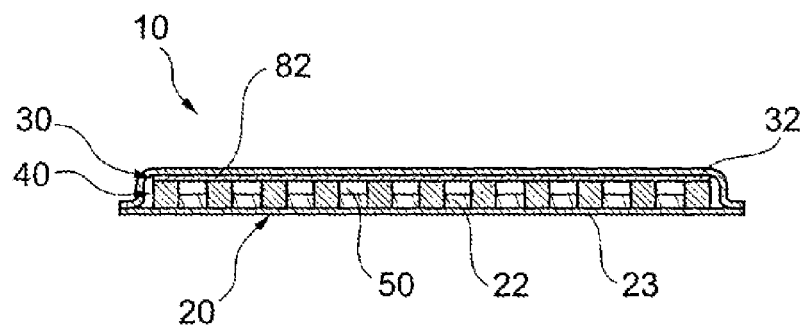
Figure 7:
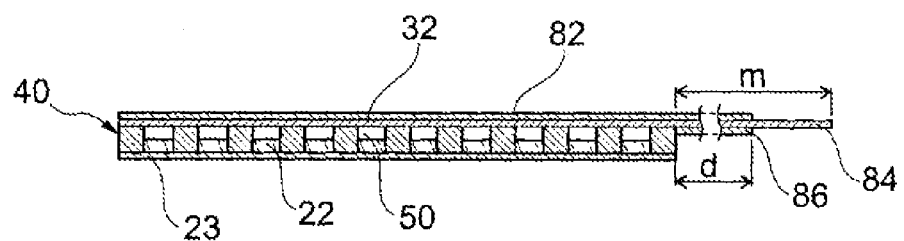
Figure 10:
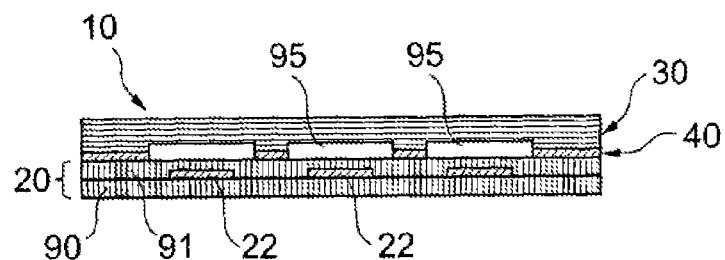
Figure 11:
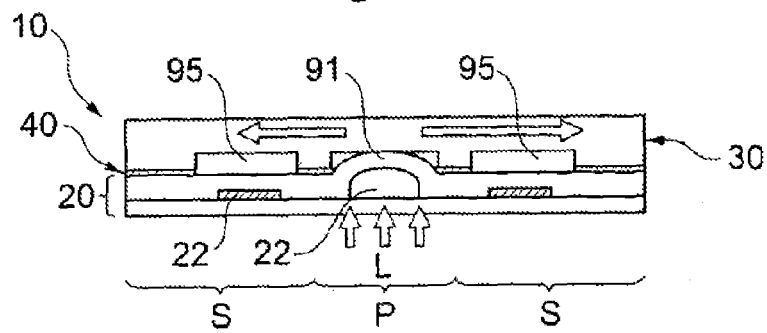
Figure 8:
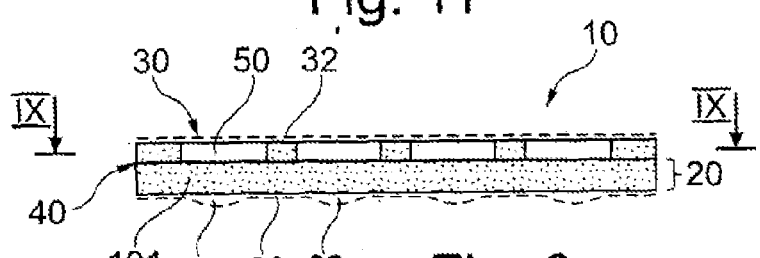
Figure 9:
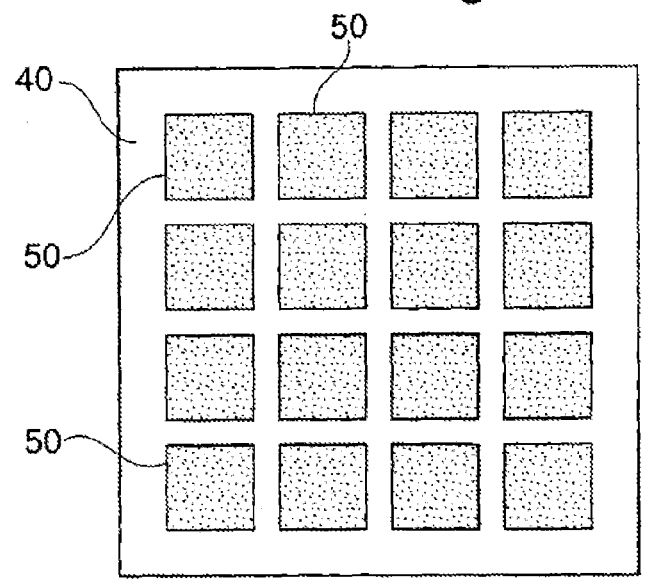
Figure 12:
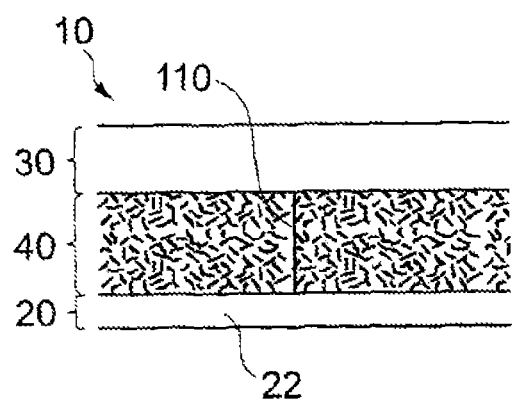
Figure 13:
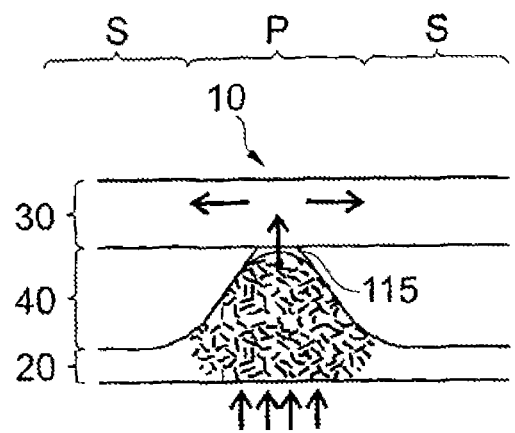
Figure 14:
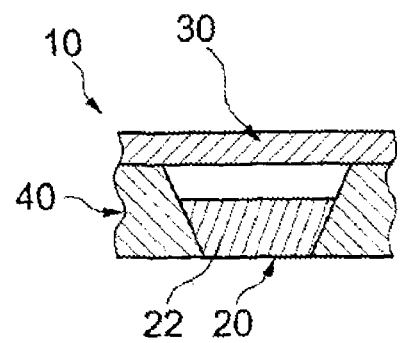
Figure 15:
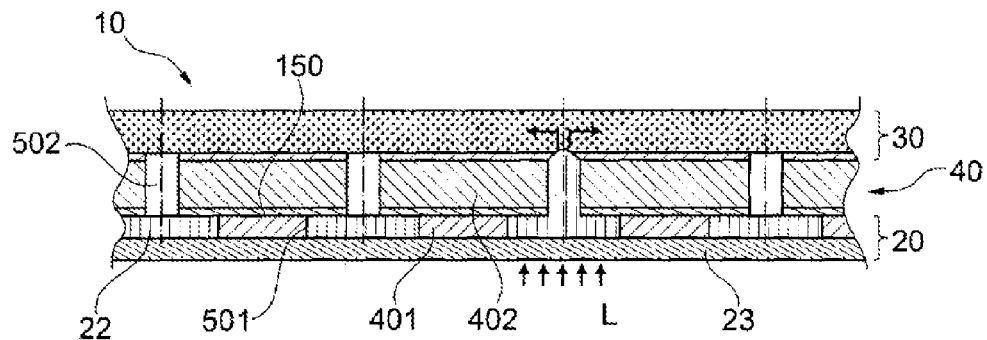
Figure 16:
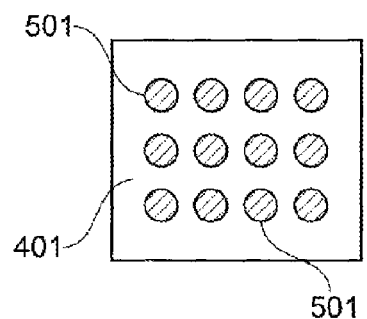
Figure 17:
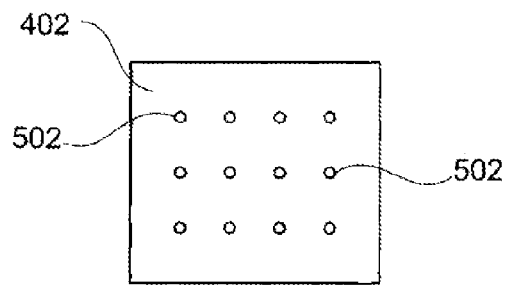

It will be possible to understand the invention more clearly on reading the detailed description that will follow, of nonlimiting examples of implementation of said invention, and on examining the appended drawings, on which:

FIG. 1 diagrammatically and partially represents an example of an item produced in accordance with the invention, FIG. 2 is a section according to II-II of FIG. 1, FIG. 3 represents a detail of FIG. 1, FIG. 4 illustrates the use of the item of FIGS. 1 to 3 in place on a wound, FIGS. 5 to 8 are views analogous to FIG. 1 of implementation variants, FIG. 9 is a section according to IX-IX of FIG. 8, FIG. 10 is a view analogous to FIG. 1 of an implementation variant, FIG. 11 illustrates the use of the item of FIG. 10, FIG. 12 is a view analogous to FIG. 1 of a variant of implementation of an item according to the invention, FIG. 13 illustrates the use of the item of FIG. 12, FIG. 14 is a view analogous to FIG. 3 of an implementation variant, FIG. 15 is a view analogous to FIG. 1 of an implementation variant, and FIGS. 16 and 17 represent, respectively, viewed from above, the layers with openings of the structure of FIG. 15.

In the figures, the actual proportions of the various constituent elements have not always been respected, in the interests of clarity of the drawing. Likewise, certain elements may have been represented with a gap although they are in reality in contact.

The item 10 according to the invention represented in FIGS. 1 to 4 is a dressing intended to be applied to a wound, but the entire description which follows is valid for items other than a dressing, in particular for a feminine hygiene item or a disposable diaper.

In the interests of simplification, the dressing has not been represented with an external protective layer in all the figures.

The item 10 comprises a proximal structure 20 intended to come into contact with the skin and the wound, while preferably being centered on the wound, a distal structure 30 and an insert structure 40.

Each of the proximal, distal and insert structures may comprise one or more constituent layers, permanently or nonpermanently assembled together, using adhesive and/or by local fusion of material. When an adhesive layer is used, it is not always represented on the drawing, in the interests of clarity.

The distal structure 30 is produced, in the example of FIGS. 1 to 4, in such a way as to absorb the liquid and to store it, with an absorption capacity which is relatively high and in particular greater than 500 g/m$^2$, or even 800 g/m$^2$. As a variant, the distal structure 30 is produced in such a way as to enable lateral migration of the liquid. This migration may take place toward a region of the item where the liquid may be discharged by evaporation, and/or toward a reservoir which is located on the side of the item, as will subsequently be explained in detail.

The insert structure 40 makes it possible to limit the exchange of liquid between the distal 30 and proximal 20 structures. The item is arranged so as to promote the exchange of liquid in the zone(s) of the item which superimpose(s) on the liquid secretion zone(s) P, and so as to reduce or better still eliminate, the exchange of liquid from the distal structure to the proximal structure in the zone(s) S which are laterally offset with respect to the liquid secretion zone(s) P.

The insert structure 40 may thus be produced so as to maintain a gap between the proximal 20 and distal 30 structures other than at the base of the liquid secretion zone(s) P.

In the example of FIGS. 1 to 4, the insert structure 40 comprises openings 50, in particular arranged like the holes of a grid, with a constant gap between the openings in two directions perpendicular to one another.

Outside the openings 50, the insert structure 40 comes into contact with the distal structure 30 according to assembly regions 52 where the insert structure 40 is, for example, attached to the distal structure 30 by adhesive bonding or welding.

The proximal structure 20 comprises a material capable of swelling in the presence of water. This material is, for example, as illustrated, present in the form of inserts 22 inserted in the openings 50. The swelling of the inserts 22 which occurs in the openings 50 in the presence of the secreted liquid allows the proximal structure 20, in the example under consideration, to undergo an expansion to the point of coming into contact with the distal structure 30, as illustrated in FIG. 4. This contact creates a fluidic bridge which allows diffusion of the liquid from the proximal structure into the distal structure 30.

In order to produce the item 10, the insert structure 40 may be produced for example in the form of a grid by punching a sheet of a hydrophobic and nonabsorbent material so as to produce the openings 50.

The inserts 22 may be produced by cutting up a sheet of a material which has the capacity to swell in the presence of water, while giving each insert a shape which is complementary to that of an opening or the very least allows the insert 22 to become at least partially housed in the opening 50. Since the thickness of the inserts 22 is less than that of the openings 50, a non-zero gap e is obtained between the free faces 20 of the inserts 22 and the distal structure 30, once the item 10 is assembled.

The inserts 22 are preferably, as illustrated, supported by a layer of interface 23 with the skin, the wound and/or the mucous membranes, extending under the insert structure 40.

During production, the inserts 22 are for example put in place on the interface layer 23 before assembly thereof with the insert structure 40.

The distal structure 30 comprises for example, as illustrated, a layer forming a reservoir 31 with an absorption capacity greater than or equal to 500 g/m$^2$, located between a transfer layer 32 and an external protective layer 33 which is, for example, impermeable to water but permeable to water vapor.

The transfer layer 32 may be adhesively bonded or assembled by other means to the insert structure 40.

During the use of the item 10, the secretion of the liquid L in at least one zone P on which the item 10 is placed leads to swelling of the insert(s) 22 which is (are) superimposed on this zone P.

The swelling of these inserts 22 causes them to expand over the entire thickness of the insert structure 40 and to come into contact with the distal structure 30, in the case in point the transfer layer 32, which leads locally to the creation of a fluidic bridge between the proximal structure 20 and the distal structure 30, as illustrated. This fluidic bridge allows a transfer of liquid from the proximal structure 20 to the distal structure 30, and, in the example under consideration, allows the layer forming a reservoir 31 to absorb the secreted liquid. Said liquid can then diffuse laterally in the distal structure 30 to at least one zone S, laterally offset from the zone P.

The liquid which accumulates in the zone S cannot return to the skin, the wound and/or the mucous membranes by redescending vertically through the item 10, owing to the presence of the air-filled space in the openings 50 between the inserts 22 which have not undergone swelling and the transfer layer 32. The item 10 thus makes it possible to keep dry the surface of the skin, the wound and/or the mutual membranes which is located in the zone S.

In order to produce the interface layer 23, an open-mesh fabric coated with a gel formed from a hydrophobic elastomeric matrix which is highly plasticized and contains a small amount of particles of a hydrocolloid, as described in Example 1 of International application WO 00/16725, may be used.

The inserts 22 are, for example, made from a water-swelling material in the form of a sheet, having for example a thickness of about 1 mm, or even a tenth of a millimeter, and are arranged on the internal face of the interface layer 23, opposite that intended to come into contact with the wound.

In order to produce the inserts 22, use may be made of a sheet material of the Novathin® brand sold by the company EAM under the reference J4000950DTNB, which is a substrate of cellulose fibers and of superabsorbent polymer having a grammage of 400 g/m$^2$ and a thickness of 1.14 mm, or the sheet material sold by the company Buckeye Steinfurt GmbH under the reference Vizorb® 3924 (180MBS3A), having a grammage of approximately 180 g/m².

In order to form the insert structure 40, several thin layers of closed-cell foam, for example 3 to 4 layers may be assembled in order to achieve a thickness greater than or equal to 3 mm. The assembly is carried out by lamination for example using a double-sided adhesive. The insert structure 40 is for example made up of three layers of a closed-cell polyethylene (PE) hydrophobic foam of the Alveolit® TEE.1000.8 brand having a thickness of 0.8 mm. The openings 50 consist for example of circular holes 5 mm in diameter, the centers of which are evenly spaced 1 cm apart in the two directions.

The transfer layer 32 is, for example, made up of a nonwoven Jettex® 1205 C from the company Orsa and the layer forming a reservoir 31 is, for example, made of a hydrophilic foam, for example a hydrophilic PU foam having the reference MCF 03 and a thickness of 4.5 mm from the company AMS.

In order to assemble the interface layer 23 with the insert structure 40, the whole assembly may, for example, be heated under pressure.

A double-sided adhesive may, for example, be used to adhesively bond the transfer layer 32 to the insert structure 40.

The adhesive bonding of the layer forming a reservoir 31 can be carried out, for example, using a 65-100° C. thermal bonding web.

In one implementation variant, the interface layer 23 is replaced with a hydrophobic nonwoven of the coverstock type (Berotex® PE-SX), previously described.

Comparative Tests

The tests are carried out at 23° C. and 33/35% hygrometry.

A comparison is made between a known dressing having the reference Urgotul Absorb® and a dressing according to the invention having the structure illustrated in FIGS. 1 to 4 and made with the following materials:

interface layer 23: according to example 1 of WO 00/16725, heat-set knit made of polyester yarns, coated with a gel formed from a highly plasticized, high-molecular-weight S-EB-S elastomeric matrix containing a dispersion of approximately 15% by weight, relative to the weight of gel, of hydrophilic particles of a hydrocolloid consisting of sodium carboxymethylcellulose, inserts 22: pellets of Novathin® J4000950DTNB, the thickness of which is approximately 1 mm, insert structure 40: Alveolit® closed-cell PE hydrophobic foam 3 mm thick, perforated as in FIG. 2, with circular holes 5 mm in diameter, the centers of which are 10 mm apart, transfer layer 32: nonwoven based on cellulose (55%) and on polyester (45%), Jettex® 1205C from the company Orsa, layer forming a reservoir 31: hydrophilic PU foam 4.5 mm thick, having the reference sign MCF 03 from the manufacturer AMS.

An inkspot may be deposited on the inserts 22, so as to, after use, determine which are those that have undergone swelling and for which the ink has been diluted.

The dressings are each placed on a sintered glass slab, by which a solution of sodium chloride at 0.83% and of calcium chloride at 0.04% (by weight) is injected.

A volume of 10 ml is injected into the dressing by means of a syringe driver connected to a sintered glass slab brought into contact with the lower face of the dressing, this sintered glass slab simulating the wound. The dressing is positioned horizontally with a weight placed at the surface of the dressing exerting a pressure of 25 mbar. The liquid injection flow, through the sintered glass slab is set at 10 µl/min.

At the end of the experiment, only the inserts in contact with the wound have undergone swelling: the ink can no longer be seen on said inserts. The inserts which are not in contact with the simulated wound retain their initial appearance. In the case of the reference dressing (Urgotul Absorb), the moist area in contact with the skin is estimated at 90 cm², whereas, for a dressing according to the invention, the moist surface area is estimated at only 7 cm², that is to say the surface area of the sintered glass slab, which demonstrates the effect with respect to the preservation of the perilesional skin. Thus, by virtue of the invention, the moist surface area in contact with the skin remains centered on the wound and the risk of leaking is in addition reduced, in particular when the dressing is not horizontal.

The results demonstrate the effectiveness of the invention, both for a dressing oriented horizontally and for a dressing oriented vertically.

The implementation variant for the item 10, represented in FIG. 5, differs from that described with reference to FIGS. 1 to 4 in that the layer forming a reservoir 31 superimposed on the insert structure 40 is replaced with a layer forming a reservoir 80 which is offset laterally and which extends for example over the entire perimeter of the insert structure 40.

The interface layer 23 can be made water-impermeable under the layer forming a reservoir 80, or a layer forming a barrier, not represented, is introduced between the two.

Figure 5:
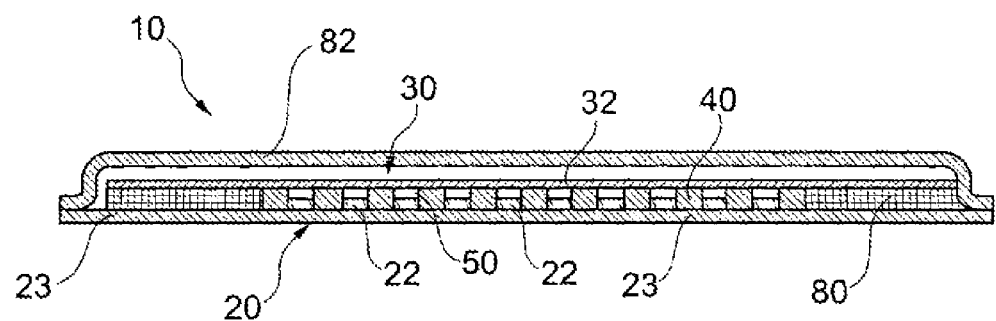

The distal structure 30 is limited in the example of FIG. 5 to the transfer layer 32, which allows the liquid that reaches it to diffuse laterally as far as the layer forming a reservoir 80.

An external protective layer 82 may cover the layer forming a reservoir 80 and may be assembled at its periphery with the interface layer 23.

The example of FIG. 5 comprises the same arrangement allowing selective triggering of the fluidic communication as in the example of FIGS. 1 to 4, i.e. inserts 22 are placed in openings 50 formed through an insert structure 40.

The thickness of the layer forming a reservoir 80 is for example, as illustrated, approximately equal to +/−20% that of the insert structure 40, so as to have an item 10 having a substantially uniform thickness.

During use, the liquid which is secreted by the wound causes the inserts 22 which are above the wound to swell, allowing contact between these inserts 22 and the transfer layer 32, then the spreading out of the liquid within said layer in the direction of the layer forming a reservoir 80, where the liquid may accumulate.

The inserts 22 which are not above the source of emission of the liquid secretions do not swell or do not swell sufficiently to come into contact with the transfer layer 32, such that the liquid which diffuses in this transfer layer 32 does not redescend toward the interface layer 23 while reaching the layer forming a reservoir 80.

The implementation variant of FIG. 6 differs from those which have just been described with reference to FIGS. 1 to 5 by virtue of the absence of a layer forming a reservoir 31 or 80, the discharging of the liquid being essentially carried out by evaporation. In this example, the protective layer 82 is permeable to water vapor and assembled at its periphery with the interface layer 23.

In the implementation variant illustrate in FIG. 7, the transfer layer 32 extends laterally, in cantilever fashion, beyond the insert structure 40, for example over a distance m equal to 20 cm, and forms a free end part 84 in contact with the ambient air.

The external protective layer 82 extends over a distance d less than m, for example of approximately 10 cm, in a mock-up produced, and covers the top of the transfer layer 32 only over a portion of its length, so as to leave the end part 84 free and to facilitate the evaporation of water at its level. An internal protective layer 86 may be present on the transfer layer 32 on the side of its lower face, so as to prevent any contact between the transfer layer 32 and the skin and/or the mucous membranes in proximity to the wound.

During the use of the item of FIG. 7, the liquid locally comes into contact with the transfer layer 32 by virtue of the fluidic bridges which form after swelling of the inserts 22 directly confronted with the secretion of the liquid, and migrates to the end part 84, where the water may evaporate.

A volume of 30 ml is injected into the dressing by means of a syringe driver connected to a frit brought into contact with the lower face of the dressing.

The liquid injection flow is set at 10 μl/min. After operation for 50 h, 28 ml of the injected liquid were evaporated, i.e. a degree of evaporation greater than 90%.

According to one variant of the present invention, a chamber is incorporated, above the transfer strip 32 or the reservoir 80, said chamber allowing the passage of air, preferably dry air, in order to increase the evaporation of the liquid present in the distal structure.

The type of dressing represented in FIG. 6, not comprising a reservoir layer within the meaning of the present invention, is particularly suitable for wounds with moderate or low exudation, for example undergoing epidermization.

For wounds which are more exudative, it is preferred to use a dressing comprising a reservoir layer, or a dressing without an absorbent layer, as represented in FIG. 7, the overflowing of the transfer strip making it possible to optimize the evaporation.

It is seen that it is thus possible to have a range of dressings, with or without reservoir layer, suitable for several types of wounds, depending on whether they are exudative or not very exudative.

The possibility for the proximal structure 20 to comprise at least one internal layer, between the inserts 22 and the insert structure 40, has been illustrated in FIG. 8. The internal layer 101 may change shape so as to accompany the swelling of the inserts 22 and allow said layer to come into contact with the distal structure 30, in the case in point limited in this example to a transfer layer 32. The inserts 22 are, for example, housed between the interface layer 23 and the internal layer 101. The inserts 22 are distributed like the openings 50 of the insert structure 40.

The liquid absorption and diffusion properties of the various layers 23 and 101 are chosen such that the migration of the liquid may take place preferentially toward the distal structure 30, at the site where the proximal structure 20 is superimposed on the liquid secretion zone(s) P. In other words, the amount of liquid which migrates laterally in the proximal structure 20 is sufficiently low or slow for the fluidic bridges between the proximal 20 and distal 30 structures to become established predominantly above the liquid secretion zone(s) P.

In one implementation example, use is made, in order to produce the interface layer 23, of a Sawabond® 4383 hydrophilic nonwoven from the company Sandler, based on PE/PET, with a grammage of 30 g/m², the inserts 22 are grains of Favor-PAC® 230 superabsorbent polymer, and the internal layer 101 is a perforated 3D film sold by the company Tredegar under the reference 40 HEX X26424. The insert structure 40 is a PE hydrophobic foam of the Alveolit® brand and the transfer layer 32 is a nonwoven based on 45% PET and 55% cellulose, the reference of which is Jetex® 1205C—from the company Orsa.

An implementation example in which the proximal structure 20 comprises first and second layers 90 and 91 having a vertical draining power, i.e. the water preferentially migrates according to the thickness of said layers, and between which is placed a water-swelling material, for example in the form of inserts 22 as described above, has been represented in FIGS. 10 and 11.

The insert structure 40 is made up of a layer of a water-impermeable adhesive, which joins together the proximal 20 and distal 30 structures. Said layer comprises cavities 95 arranged opposite the inserts 22. The second layer 91 is able to change shape and may, during the swelling of the underlying insert 22, as illustrated in FIG. 11, in the presence of liquid, come into contact with the bottom of the cavity 95. This contact allows the transfer, by capillary action or diffusion, of the liquid of the proximal structure 20 to the distal structure 30, it being possible for the liquid, once in the distal structure 30, to diffuse laterally so as to accumulate within said structure.

FIGS. 12 and 13 aim to illustrate the fact that the item can be produced in such a way that, after swelling of the water-swelling material on contact with the liquid, direct contact between the proximal 20 and distal 30 structures does not take place, but a fluidic bridge may nevertheless become established owing to the fact that the proximal 20 and distal 30 structures move closer together.

In FIG. 12, the item has been represented before it has been placed in the presence of the liquid, and in FIG. 13, the item has been represented after localized swelling of the proximal structure 20. It is seen in this example that the insert structure 40 is capable of changing shape so as to accompany the expansion of the proximal structure 20. In the initial state, before the item is placed in the presence of the liquid, the thickness of the insert structure prevents the establishment of a fluidic bridge between the proximal and distal structures. When the insert structure is locally compressed by the expansion of the proximal structure, the proximal and distal structures are sufficiently close together for it to be possible for a transfer of liquid from the proximal structure to the distal structure to be established by capillary action. In this example, the insert structure 40 is for example a flexible and nonabsorbent hydrophobic material based on polymers, for instance polyolefins, such as polyethylene or polyphenylene ether or ethylene vinyl acetate, in which slits 110, preferably in the form of lattice work viewed from above, are made, such that a slot may open up when the material undergoes bending. The material may for example be in the form of a flexible film. An opening 115 is then created locally in the insert structure 40, to which the liquid may flow from the proximal structure to the distal structure. In the adjacent zones, less subjected to bending, the slits do not open sufficiently to allow the establishment of a fluidic bridge between the proximal and distal structures, thus blocking the passage of the liquid from the distal structure to the proximal structure.

The use of such materials makes it possible to produce an insert structure without openings. Such a material may also, according to another variant of the present invention, replace the air in the cavities of the insert structure between the swelling element and the distal structure in the variants described for example with reference to FIGS. 1 to 8. These materials may also be used to fill the cavities of FIGS. 10 and 11 and to thus optimize the operation of the item by eliminating any risks of liquid return to the wound, the skin or the mucous membranes during the lateral migration of the liquid in the distal layer. This may also make it possible to produce cavities of small thickness in the distal layer and to promote the obtaining of a thin item. It may be advantageous for the inserts 22 to have a shape which promotes their expansion in the direction of the distal structure 30 rather than toward the surface on which the item 10 is applied. FIG. 14 illustrates the possibility of producing the proximal structure 20 in the form of inserts 22 which are trapped in the openings 50 of the insert structure 40, the cross section of the openings 50 becoming narrower the further away it is from the distal structure 30 and the inserts 22 having a complementary shape, such that, mechanically, the expansion of the inserts toward the surface on which the item is placed is impeded.

In all of FIGS. 15 to 17, the item comprises an insert structure 40 comprising two layers 401 and 402 superimposed on one another, with optionally, as illustrated, interposition of an adhesive layer 150 between the two. The layers 401 and 402 comprise respective openings 501, 502.

The openings 501 of the lower layer 401, adjacent to the interface layer 23, have a cross section, in a plane parallel to the proximal structure 20, greater than those of the openings 502 made in the upper layer 402, the latter being adjacent to the distal structure 30.

Inserts 22, comprising a material capable of swelling in the presence of water, are placed in the openings 501 of the lower layer 401. Preferably, the openings 502 of the upper layer 402 do not initially contain such inserts. Thus, a function of the upper layer 402 is to keep each insert 22 in an opening 501 of the lower layer 401.

As is represented in FIG. 15, when an insert 22 is dry, it is kept between the interface layer 23 and the upper layer 402, owing to the reduction in the cross section of the openings between the lower layer 401 and the upper layer 402.

When an insert 22 is placed in contact with the liquid, the material that it comprises gradually swells, and extends through the openings 502 of the upper layer 402, so as to reach the distal structure 30.

The process for producing such an item makes it possible to keep the inserts 22 of the lower layer 401 against the interface layer 23 without requiring the use of an adhesive in contact with the inserts 22, which is advantageous.

The openings 501 of the lower layer 401 preferably have a diameter (or a largest dimension) of between 5 and 25 mm, for example 8 mm, while the openings 502 of the upper layer 402 have a diameter (or a largest dimension) of between 1 and 10 mm, for example 3 mm.

In one implementation example, each layer 401 or 402 is made of hydrophobic foam, for example having the reference TEE 10008. The water-swellable composition of the inserts 22 is composed of the following constituents (the percentages are weight fractions).

| Constituents | (by weight) % |
|---|---|
| 1 Absolute ethanol | 51.903 |
| 2 PVP K30 (BASF) | 4.152 |
| 3 Klucel MF pharm (HERCULES) | 1.038 |
| 4 Favor PAC 230 (EVONIK) | 41.523 |
| 5 Glycerol 4810 | 1.384 |

It is advantageous for the material capable of swelling in the presence of water to be in the form of a water-swellable paste comprising, by weight, from 10% to 90% of water-expandable polymer, in particular based on SAP particles (for example Favor PAC 230 from Evonik),
from 1% to 20% of water-soluble binders, for example based on polyvinylpyrrolidone (for example Kollidon 30 from BASF) and/or on hydroxypropylcellulose (for example Klucel MF Pharm from Hercules),
from 0% to 20% of glycerol,
from 30% to 80% of homogenization liquid, for example based on alcohol, for example ethanol.

Having a water-swellable material in the form of a paste enables easier handling during production.

The invention is not limited to the examples described, and the implementation features illustrated in the figures may be combined in variants which are not represented.

The interface layer and/or all the other layers of the item may comprise, in particular in the case of a dressing, one or more active agents such as substances which promote healing or biocidal substances, hemostatic or anti-inflammatory compounds, and also optionally a fragrance, an anti-odor agent or a deodorant. In one variant which is not illustrated, the end part 84 of the example of FIG. 7 is connected via one face to an offset layer forming a reservoir. The expression "comprising one" should be understood as being synonymous with "comprising at least one" and the expression "between" should be understood to mean limits included, unless otherwise specified.

The invention claimed is:

1. An item having liquid storage and/or discharge properties, comprising:
a liquid-permeable proximal structure which is proximal with respect to a liquid emission zone, comprising a material capable of swelling in the presence of a liquid,
a distal structure which is distal with respect to the liquid emission zone, capable of draining the liquid,
a hydrophobic and nonabsorbent insert structure extending between the distal and proximal structures, and being capable of locally limiting, when said material is not swollen, the exchange of liquid between the distal and proximal structures by maintaining a gap between these structures, and of allowing a local expansion of the proximal structure in at least one zone where said material is swollen in response to coming into contact with the liquid, this expansion causing the proximal structure and the distal structure to move closer together locally and the transfer of said liquid from this zone of the proximal structure having undergone expansion to the distal structure.

2. The item as claimed in claim 1, the proximal structure having a non-uniform distribution of the material capable of swelling.

3. The item as claimed in claim 1, the insert structure having openings, the expansion of the proximal structure at least partially taking place in an opening of the insert structure.

4. The item as claimed in claim 3, the distribution of the openings being substantially the same as that of the material capable of swelling.

5. The item as claimed in claim 1, the insert structure being a closed-cell hydrophobic alveolar material.

6. The item as claimed in claim 1, the insert structure comprising a slot capable of opening up when said structure undergoes bending.

7. The item as claimed in claim 1, the material capable of swelling being chosen from:
a material comprising at least one superabsorbent polymer, itself chosen from particles of superabsorbent polymers or nonwovens based on cellulose fibers and on particles of a superabsorbent polymer, a water-swelling alveolar material.

8. The item as claimed in claim 1, the proximal structure comprising an interface layer intended to come into contact with the liquid emission zone.

9. The item as claimed in claim 8, the interface layer being chosen from nonabsorbent textile materials.

10. The item as claimed in claim 1, the insert structure providing the attachment of the proximal structure to the distal structure so as to make at least one opening where the swelling of the material of the proximal structure results in a transfer of the liquid to the distal structure by contact between the proximal structure and the distal structure.

11. The item as claimed in claim 1, the proximal structure being entirely located outside the insert structure in the absence of swelling of the material capable of swelling.

12. The item as claimed in claim 1, the proximal structure being inserted in the insert structure in the absence of swelling of the material capable of swelling, and extending over only a part of the thickness thereof.

13. The item as claimed in claim 1, the proximal structure comprising or being made up of inserts of the material capable of swelling, the insert structure having a sufficient thickness so that, before swelling, the inserts do not come into contact with the distal structure.

14. The item as claimed in claim 13, the inserts being borne by an interface layer.

15. The item as claimed in claim 1, the distal structure comprising at least one cavity which opens out in the direction of the proximal structure, this cavity being at least partially superimposed on a zone of the proximal structure where the swelling is liable to take place.

16. The item as claimed in claim 1, the insert structure comprising two layers with openings, including one lower layer on the side of the proximal structure and one upper layer on the side of the distal structure, the openings of the upper layer having a smaller cross section than the openings of the lower layer, and being superimposed on the latter, the material capable of swelling being at least partially contained, when dry, in the openings of the lower layer.

17. The item as claimed in claim 16, the material capable of swelling totally filling the openings of the lower layer.

18. The item as claimed in claim 16, the openings of the lower layer having a larger dimension of between 5 and 25 mm and the openings of the upper layer having a larger dimension of between 1 and 10 mm.

19. The item as claimed in claim 16, the material capable of swelling being retained in the openings of the upper layer without the use of adhesive on the side of the proximal structure.

20. The item as claimed in claim 1, the material capable of swelling being pasty, at least during the preparation of the item.

21. The item as claimed in claim 20, the material capable of swelling comprising a water-expandable polymer and a water-soluble binder.

22. The item as claimed in claim 21, the material capable of swelling having the following formulation, by weight relative to the total weight of the mixture:

from 10% to 90% of water-expandable polymer(s),
from 1% to 20% of water-soluble binder(s),
from 0% to 20% of glycerol, and
from 30% to 80% of homogenization liquid.

23. The item as claimed in claim 1, the distal structure comprising a plurality of cavities arranged according to a matrix distribution.

24. The item as claimed in claim 1, the distal structure comprising a layer forming a reservoir, having a liquid absorption capacity greater than or equal to 500 $g/m^2$.

25. The item as claimed in claim 1, the distal structure being formed from a transfer layer and being devoid of a layer forming a reservoir having a liquid absorption capacity greater than or equal to 800 $g/m^2$.

26. The item as claimed in claim 1, the item comprising an offset layer forming a reservoir which is laterally offset with respect to the insert structure, and the distal structure comprising a transfer layer connected to the offset layer forming a reservoir.

27. The item as claimed in claim 1, comprising a transfer layer having a free end part from which the liquid may evaporate, the transfer layer being partially superimposed on the insert structure.

28. The item as claimed in claim 1, further defined as a dressing.

29. The item as claimed in claim 7, wherein the water-swelling alveolar material is a hydrophilic polyurethane foam.

* * * * *

UNITED STATES PATENT AND TRADEMARK OFFICE
CERTIFICATE OF CORRECTION

| | | |
|---|---|---|
| PATENT NO. | : 9,474,661 B2 | Page 1 of 1 |
| APPLICATION NO. | : 14/416928 | |
| DATED | : October 25, 2016 | |
| INVENTOR(S) | : Yves Fouillet et al. | |

It is certified that error appears in the above-identified patent and that said Letters Patent is hereby corrected as shown below:

On the Title Page

Item (71) Applicants, Line 4:

Delete "LABORATORIES URGO, Chenove" and replace with -- LABORATOIRES URGO, Chenôve --.

Item (72) Inventors, Line 3:

Delete "Frederic" and replace with -- Frédéric --.

Signed and Sealed this
Thirty-first Day of January, 2017

Michelle K. Lee
*Director of the United States Patent and Trademark Office*